United States Patent [19]
Wolfbeis et al.

[11] Patent Number: 6,001,999
[45] Date of Patent: Dec. 14, 1999

[54] LUMINESCENCE INDICATOR INCLUDING IONOPHORIC MOIETY

[75] Inventors: Otto S. Wolfbeis; Jörg Daub; Thomas Gareis; Matthias Kollmannsberger, all of Regensburg; Stefan Heinl, Neutraubling; Tobias Werner, Regensburg; Christian Huber, Abensberg, all of Germany; Andrei Boila-Göckel; Marco Jean Pierre Leiner, both of Graz, Austria

[73] Assignee: AVL Medical Instruments, Schaffhausen, Switzerland

[21] Appl. No.: 09/085,812

[22] Filed: May 27, 1998

[30] Foreign Application Priority Data

May 30, 1997 [AT] Austria ........................ 929/97

[51] Int. Cl.$^6$ ................... C07D 419/02; C07D 209/56
[52] U.S. Cl. .................. 540/468; 540/469; 540/472; 548/110; 548/405; 544/229; 544/106; 544/336
[58] Field of Search ..................... 540/468, 469, 540/472; 544/229, 106, 336; 548/410

[56] References Cited

U.S. PATENT DOCUMENTS

| | | | |
|---|---|---|---|
| 4,774,339 | 9/1988 | Haugland et al. | 548/405 |
| 5,162,525 | 11/1992 | Masilamani et al. | 540/468 |
| 5,187,288 | 2/1993 | Kang et al. | 548/110 |
| 5,248,782 | 9/1993 | Haugland et al. | 548/110 |
| 5,274,113 | 12/1993 | Kang et al. | 548/405 |
| 5,433,896 | 7/1995 | Kang et al. | 252/700 |
| 5,439,828 | 8/1995 | Masilamani et al. | 436/74 |
| 5,451,663 | 9/1995 | Kang et al. | 530/367 |
| 5,516,911 | 5/1996 | London et al. | 548/236 |

OTHER PUBLICATIONS

R. Crossley, et al., "Synthesis and Properties of a Potential Extracellular Fluorescent Probe for Potassium", J. Chem. Soc. Perkin Trans. 2, pp. 1615–1622 (1994).

M.R. Angelastro et al., J. Med. Chem. vol. 37, pp. 4538–4553 (1994).

J.R. Lakowicz, "Topics in Fluorescence Spectroscopy", vol. 4: Probe Design and Chemical Sensing, pp. 133–134 (Plenum Press, New York & London) (1994).

Frank Kastenholz, Inaugural Dissertation, University of Cologne, Fig. 32, p. 54 (1993).

M.J.P. Leiner, P. Hartmann, "Theory and Practice in optical pH sensing", Sensors and Actuators B, 11, pp. 281–289 (1993).

H. Wang, D.D. Weller, "Solid Phase Synthesis of Neutral Oligonucleotide Analogues",Tetrahedron Letters, vol. 32, No. 50, pp. 7385–7388 (1991).

A.P. de Silva et al., "A New Benzo–Annelated Cryptand and a Derivative with Alkali Cation–Sensitive Fluorescence", Tetrahedron Letters, vol. 31, No. 36, pp. 5193–5196 (1990).

B. Dietrich, et al., Tetrahedron vol. 29, pp. 1629–1645 (1973).

W.O. Foye, L.R. Fedor, Jr., "The Preparation of Oxidized Derivatives of 1–Ethylsulfonyl–4–ethylpiperazine", Journal of the American Pharmaceutical Association, vol. 48, No. 7, pp. 412–414 (1959).

CA 99:177723h. (1983).

*Primary Examiner*—Richard L. Raymond
*Assistant Examiner*—Pavanaram K Sripada
*Attorney, Agent, or Firm*—Baker & Botts LLP

[57] ABSTRACT

The invention relates to a compound having the general Formula I

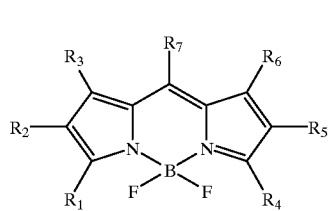

(I)

in which one of the groups $R_1, R_2, R_3, R_4, R_5, R_6$ and $R_7$ represents an ionophoric moiety and the remaining groups each independently are hydrogen, a lipophilic or hydrophilic group or a reactive group for coupling to a polymer or a biomolecule, or $R_2$ forms an aromatic ring system together with $R_3$ and $R_5$ forms an aromatic ring system together with $R_6$.

the compound of the invention is useful as a luminescence indicator for cations.

13 Claims, 6 Drawing Sheets

C1

C2

C3

C4

C5

LUMINESCENCE INDICATOR INCLUDING IONOPHORIC MOIETY

BACKGROUND OF THE INVENTION

The present invention relates to luminescence indicators for determining cations, in particular alkali ions and H$^+$ ions (pH value), of liquid, in particular aqueous, media. In effecting such determination, the substance to be determined (=analyte) is contacted with a luminescence indicator (=luminophore-ionophore) having a luminophoric moiety and an ionophoric moiety, which ionophoric moiety reacts with the analyte present in the sample, wherein the luminophoric moiety changes its luminescence properties, after which the luminescence is measured and the concentration and activity of the analyte are deduced, i.e. the cation is determined, utilizing the test reading.

A determination method of this type is based on the so-called "PET effect". This latter term denotes the transfer, induced by photons, of electrons (photoinduced electron transfer=PET) from the ionophoric moiety or ionophore, respectively, to the luminophoric moiety or luminophore, respectively, which leads to a decrease in the (relative) luminescence intensity and the luminescence decay time of the luminophore. Absorption and emission wavelengths, however, remain basically unaffected in the process (J. R. Lakowicz in "Topics in Fluorescence Spectroscopy", Volume 4: Probe Design and Chemical Sensing; Plenum Press, New York & London (1994)).

By the binding of ions to the ionophore, the PET effect is partly or completely inhibited, so that there is an increase in the luminescence of the luminophoric moiety. Hence, the concentration or the activity of the ion to be determined can be deduced by measuring the change in luminescence properties, i.e. luminescence intensity and/or luminescence decay time.

From U.S. Pat. No. 5,516,911, fluorescence indicators for determining intracellular calcium are known which carry fluorescent substituents capable of acting as optical indicators.

A determination method is also known from U.S. Pat. No. 5,439,828, where diaza-cryptands are utilized as the luminophore-ionophore, which diaza-cryptands have been functionalized as fluorophores with fluorescent coumarins and, depending on their structure, are selective for lithium, sodium or potassium ions. It is stated that these luminophore-ionophores can be used in sample media of neutral pH and are even the preferred choice in such systems.

Yet, research (Frank Kastenholz, Inaugural Dissertation, University of Cologne, 1993, FIG. 32, p. 54) has shown that in the physiological pH range the fluorescence signal depends significantly on the pH of the sample and increases considerably with decreasing pH, even from pH 7.4 onwards. This affects the accuracy of a determination carried out in a biological sample. Moreover, the compounds that are being used have the disadvantage that the employed coumarins show absorption wavelengths of about 336 nm and hence cannot be excited by commercial LEDs.

These disadvantages also apply to the luminophore-ionophores mentioned in U.S. Pat. No. 5,162,525.

From Tetrahedron Letters, Volume 31, No. 36, pp. 5193–5196 (1990), diaza-cryptands are known in which the two nitrogen atoms are bound to a respective aromatic ring each, i.e. are aryl nitrogens and aniline-type nitrogens, respectively. Research conducted by the applicant has shown that these diaza-cryptands are not suited for determining potassium ions if they are present in the physiological range of concentration and at physiological pH values of the blood (7.0–7.6).

SUMMARY OF THE INVENTION

U.S. Pat. No. 4,774,339, U.S. Pat. No. 5,187,288, U.S. Pat. No. 5,274,113 and U.S. Pat. No. 5,248,782 describe fluorescent dyes containing dipyrrometheneboron difluoride as the parent substance and its derivatives with reactive substituents for covalent binding to biomolecules.

From U.S. Pat. No. 5,433,896, fluorescent dyes are known which contain 1-[isoindolyl]methylene-isoindiol as the parent substance.

Dye-conjugates of dipyrrometheneboron difluoride, wherein at least one of the reactive substituents covalently binds a dye molecule to a specific binding pair member, f.i. a nucleotide or a protein, are described in U.S. Pat. No. 5,451,663.

The present invention has as its object to make available luminophore-ionophores which lack significant dependence of the luminescence properties on the pH value of the sample at physiological pH values and thus are suited for determination in biological samples.

Further, the method of the invention is to be particularly well suited for practice in the presence of physiological concentrations of alkali ions, i.e. it should exhibit a strong dependence of the luminescent signal on the concentration of the alkali ion being determined.

This object is achieved in that the indicator that is used is a compound of the general Formula I

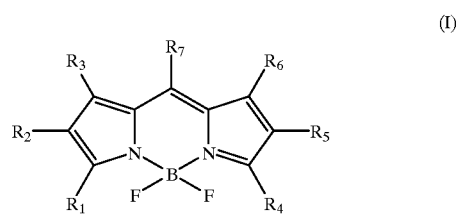

(I)

in which one of the groups $R_1, R_2, R_3, R_4, R_5, R_6$ and $R_7$ represents an ionophoric moiety and the remaining groups each independently are hydrogen, a lipophilic or hydrophilic group or a reactive group for coupling to a polymer or a biomolecule, or $R_2$ forms an aromatic ring system together with $R_3$ and $R_5$ forms an aromatic ring system together with $R_6$.

BRIEF DESCRIPTION OF THE DRAWINGS

Further objects and advantages of the present invention will be more fully appreciated from a reading of the detailed description when considered with the accompanying drawings wherein.

Figure 1:
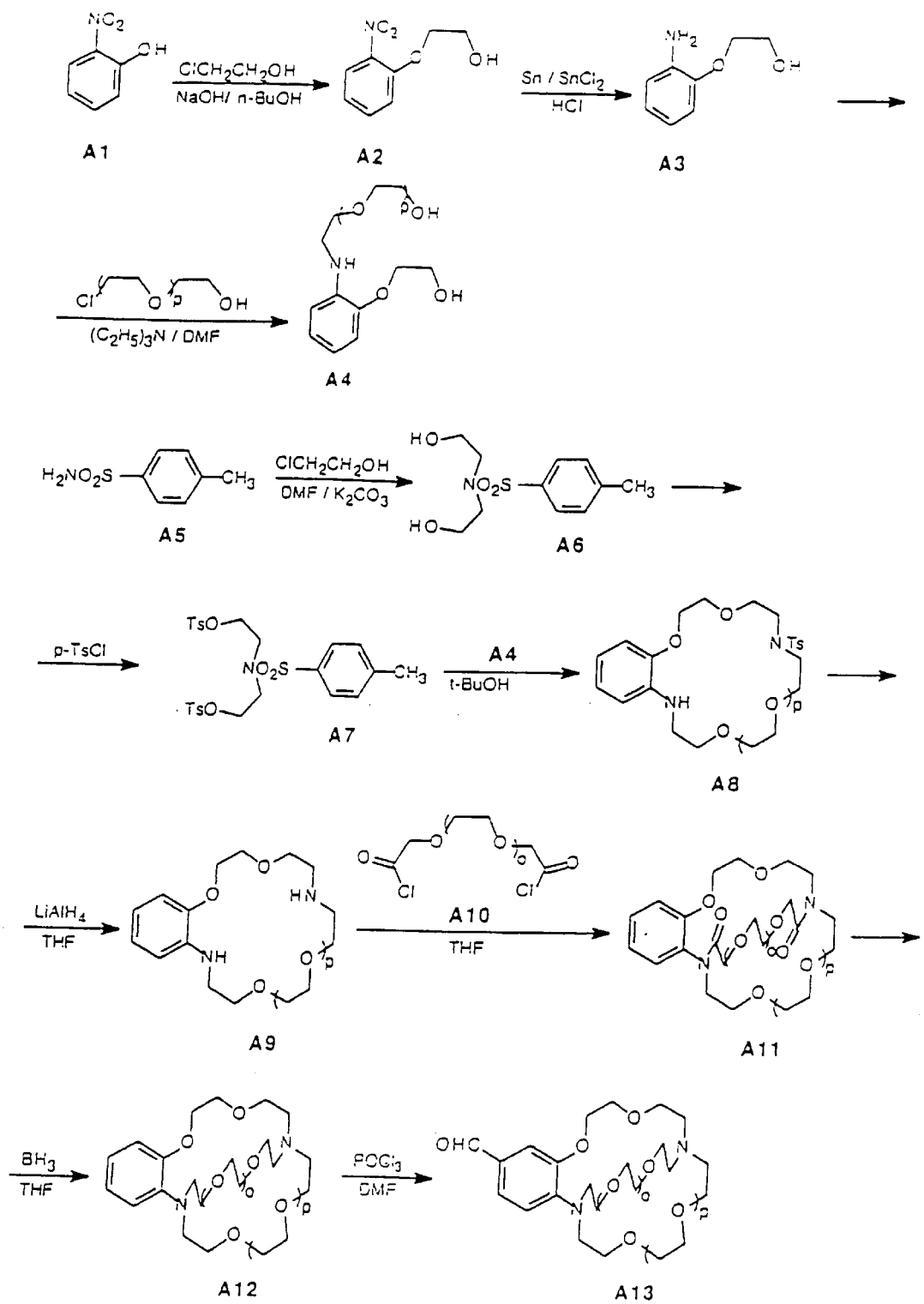
FIG. 1 is an illustration of a synthetic pathway for the ionophoric moiety of the diaza-cryptands in accordance with the invention.
Figure 2:
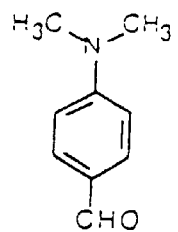
FIG. 2 is an illustration of various starting products used in preparing compounds according to the invention.
Figure 2:
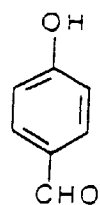
Figure 2:
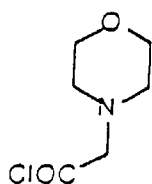
Figure 2:
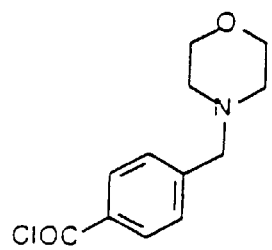
Figure 2:
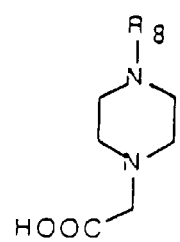
Figure 3:
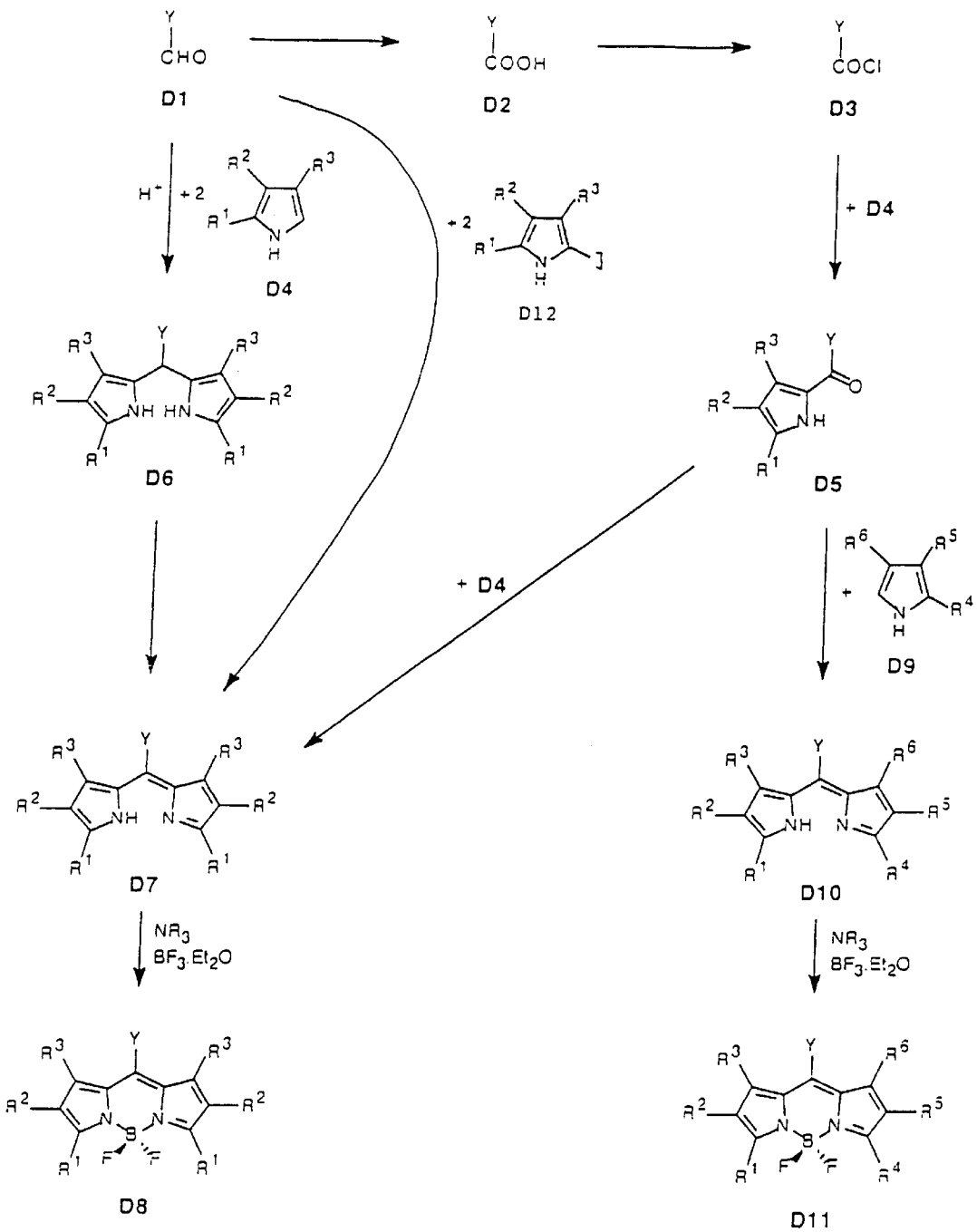
FIG. 3 is an illustration of a synthetic pathway for the preparation of dipyrromethene compounds in accordance with the invention.
Figure 4:
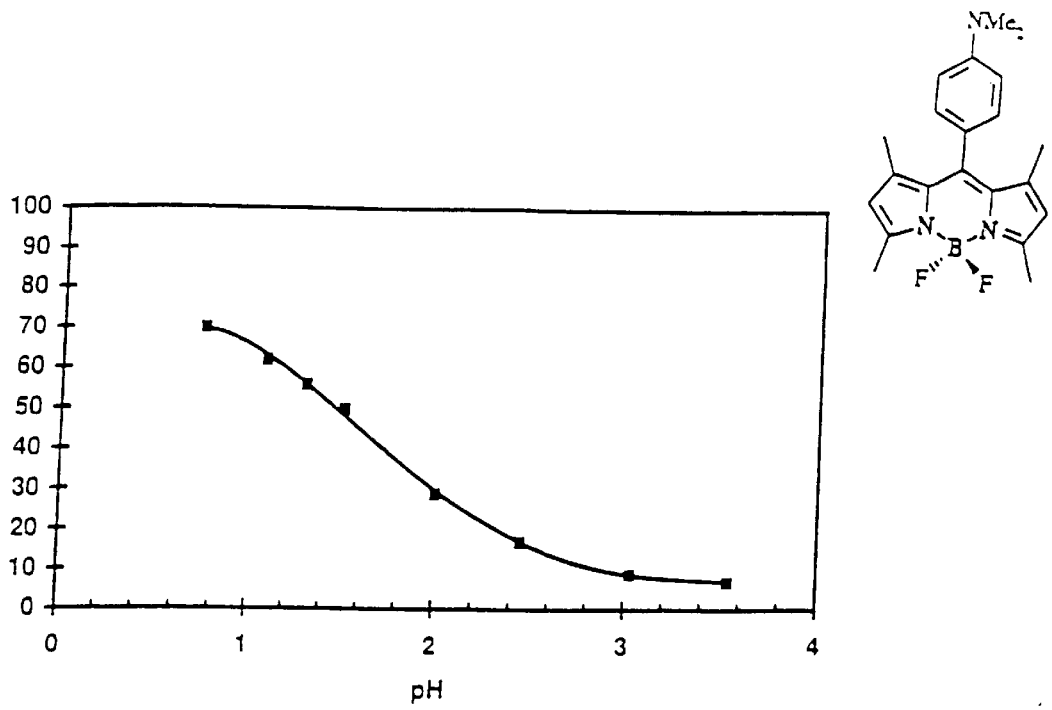
FIG. 4 is a graph illustrating the luminescence properties versus pH of a 4,4-difluoro-4-bora-3a,4a-diaza-s-indacene compound wherein the ionophoric moiety is 4-dimethylamino-phenyl in accordance with the invention.
Figure 5:
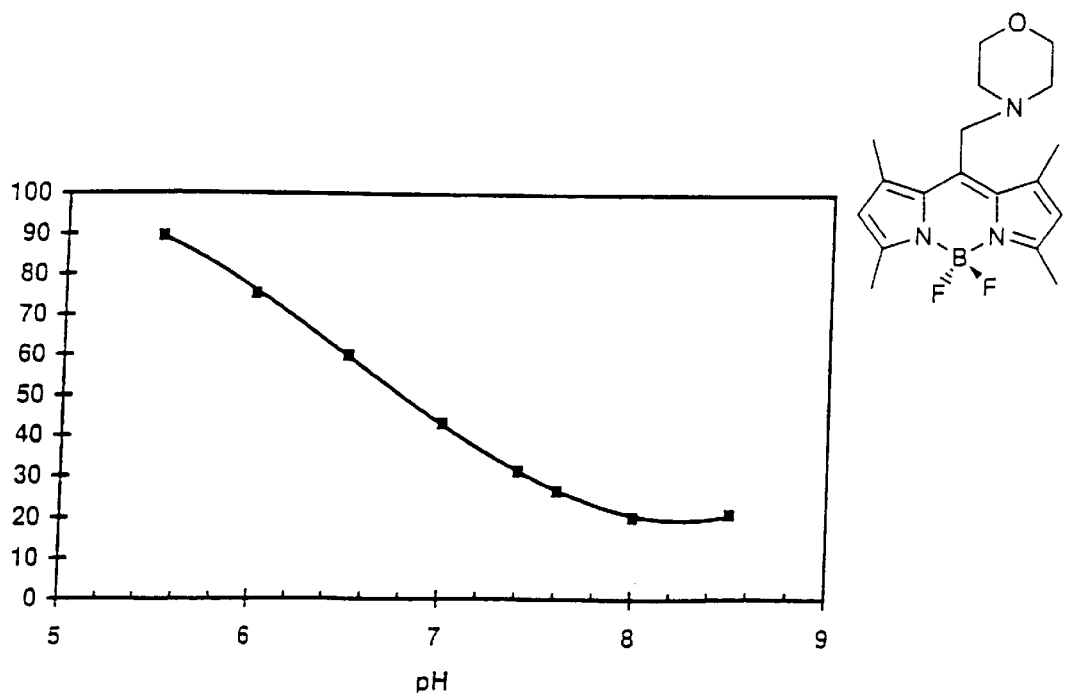
FIG. 5 is a graph illustrating the luminescence properties versus pH of a 4,4-difluoro-4-bora-3a,4a-diaza-s-indacene compound wherein the ionophoric moiety is —(CH$_2$)-morpholino in accordance with the invention.
Figure 6:
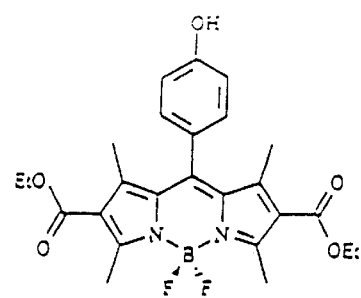
FIG. 6 is a graph illustrating the luminescence properties versus pH of a 4,4-difluoro-4-bora-3a,4a-diaza-s-indacene derivative wherein the ionophoric moiety is 4-hydroxyphenyl in accordance with the invention.
Figure 6:
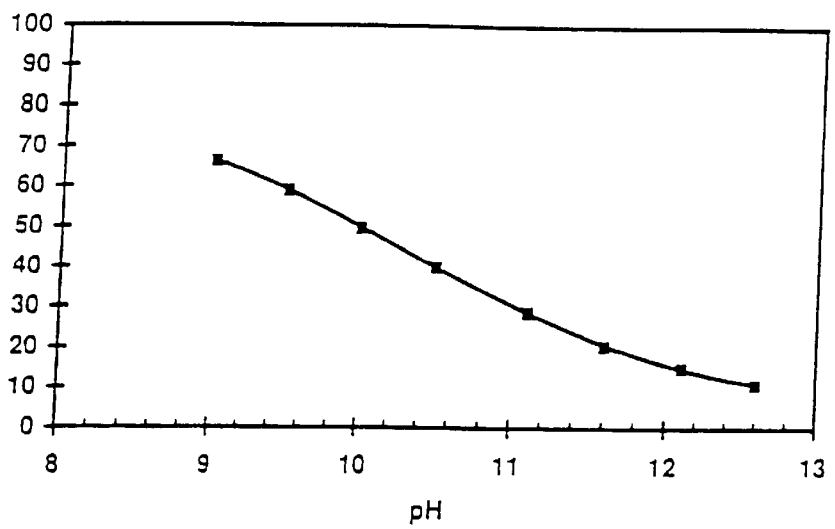
Figure 7:
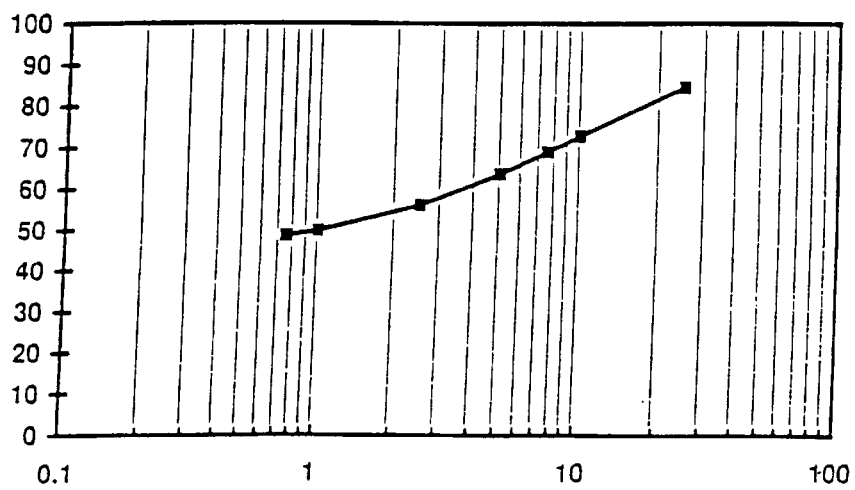
FIG. 7 is a graph illustrating the luminescence properties versus concentration of potassium ions of a 4,4-difluoro-4-bora-3a, 4a-diaza-s-indacene derivative wherein the ionophoric moiety is a cryptand in accordance with the invention.
Figure 8:
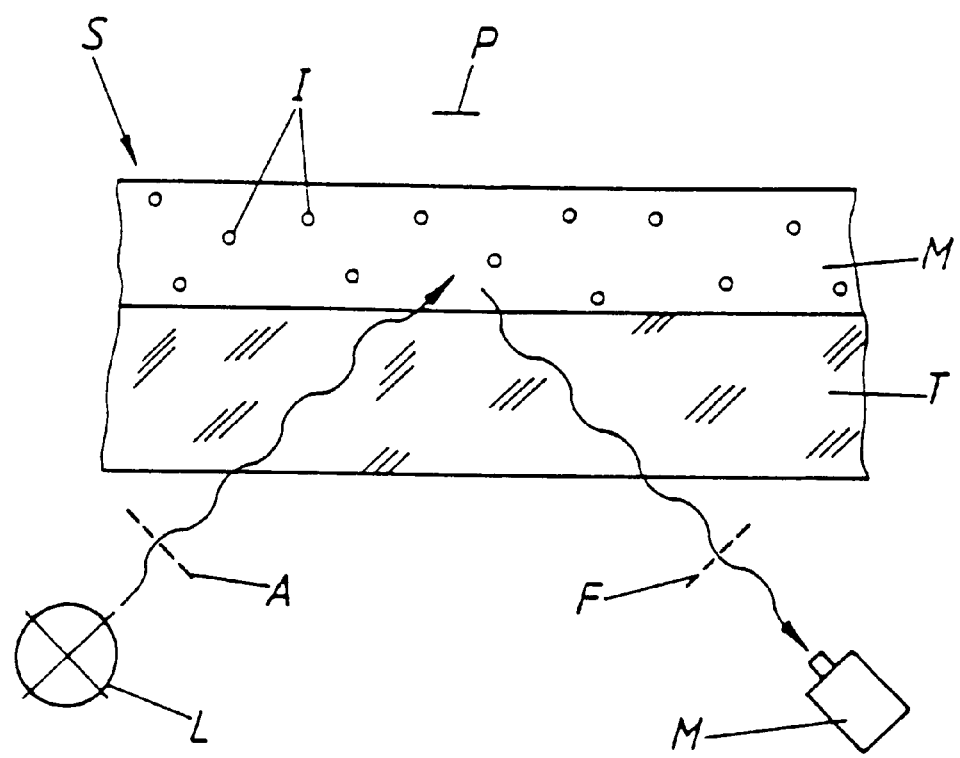
FIG. 8 is a schematic of a luminescence measuring system in accordance with the invention.

Suitable lipophilic groups would f.i. be substituted and unsubstituted alkyl groups and alkoxy groups having up to 20 C atoms.

Suitable hydrophilic groups would be alkyl groups having 1–17 C atoms and at least one hydroxyl group, and/or functional groups which at the pH of the measuring solution are present in a dissociated condition, such as f.i. carboxylic acids, sulfonic acids and phosphoric acids.

Reactive groups f.i. for coupling to aminofunctionalized polymers, f.i. aminocellulose and aminofunctional polyacrylamides, are known f.i. from U.S. Pat. No. 4,774,339, Table 4.

The reactive groups include succinimidyl esters, anhydrides, acyl azides, isocyanates, sulfonyl chlorides, sulfonyl fluorides, hydrazines, amines, haloacetamides and alcohols.

It is preferred that $R_7$ represent the ionophoric moiety and it is preferred that $R_3$ and $R_6$ be independently hydrogen or methyl.

It is preferred that the groups $R_1$ and $R_4$ represent a lipophilic group, in particular a tert. butyl each.

The following substitution patterns are particularly preferred for the compound of the invention having the general Formula I:

Pattern 1:

$R_7$: ionophoric moiety;

$R_1$, $R_4$: lipophilic group, preferably t-butyl;

$R_3$, $R_6$: independently —CH$_3$ or H;

$R_2$ or $R_5$: acid group, preferably propionic acid group for immobilization;

Pattern 2:

$R_7$: ionophoric moiety;

$R_1$, $R_4$: lipophilic group, preferably t-butyl;

$R_3$: independently —CH$_3$ or H;

$R_6$: acid group, preferably propionic acid group for immobilization;

Pattern 3:

$R_7$: ionophoric moiety;

$R_1$: lipophilic group, preferably t-butyl;

$R_3$, $R_4$, $R_6$: independently —CH$_3$ or H;

$R_5$: acid group, preferably propionic acid group for immobilization.

In the compound of the invention of the general Formula I, it is preferred that the ionophoric moiety be a diaza-cryptand having the general Formula II

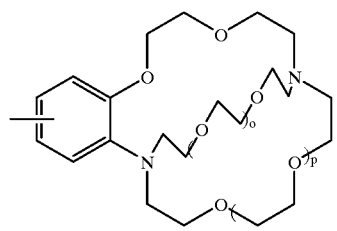

in which o and p independently mean the number 0, 1 or 2, or be one of the following groups ($R_8$=alkyl with 1–20 C atoms)

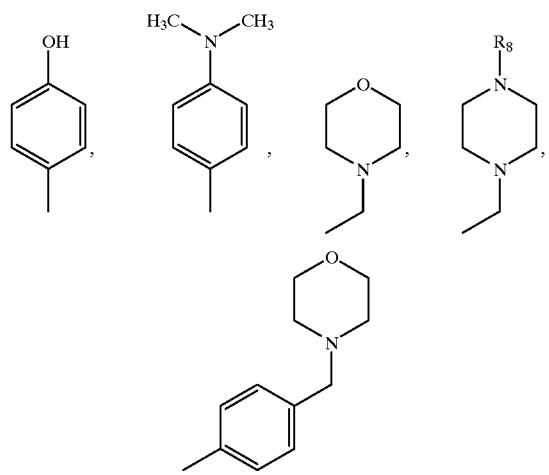

In the general Formula II, the horizontal line drawn on the benzene ring is intended to symbolize the covalent chemical bond through which the ionophoric moiety is bound directly to the compound of the general Formula I. That bond may be present in ortho position, the two meta positions or in para position to the nitrogen.

These new luminophore-ionophores have been found to be very useful for determining cations, especially alkali ions at a physiological pH and at physiological concentrations, and of H$^+$ ions (pH).

Also, the diaza-cryptands of the invention having the general Formula II have been found to be particularly useful for determining lithium ions in the concentration range between 0.30 and 2.1 mmol/l and potassium ions in the concentration range between 1.5 and 8.0 mmol/l.

Suitable luminophoric moieties would be all those moieties by which in combination with the skeleton of the general Formula I a PET effect can be achieved. A great number of ionophoric moieties is known from literature which in combination with the ionophore give a PET effect or in principle are suited for this purpose. By coupling these known ionophoric moieties to the above skeleton of the general Formula I, new compounds are obtained which may be examined by the man skilled in the art in order to find out whether a PET effect can be obtained.

Those skilled in the art will be aware that in order for a PET effect to materialize it is essential in particular that the electron donor of the ionophoric moiety be electronically decoupled from the electronic system of the luminophoric moiety (skeleton of the general Formula I). Electronic decoupling can be recognized f.i. from the fact that there is no significant change concerning the wavelengths of the absorption and emission spectra of the luminophoric moiety.

For determining lithium ions, a diaza-cryptand of the general Formula II is preferably utilized in which o and p mean the numbers 0 and 0, respectively.

For determining sodium ions there is preferably utilized a diaza-cryptand of the general Formula II in which o and p mean the numbers 0 and 1, respectively, or the numbers 1 and 0, respectively.

For determining potassium ions, a diaza-cryptand of the general Formula II is preferably utilized in which o and p mean the numbers 1 and 1, respectively.

In the following, the invention will be described in greater detail by means of examples, wherein there will be explained the synthesis and properties of some preferred indicators. Other indicators in accordance with the invention can be prepared in analogous manner by the person skilled in the art.

1. Synthesis of precursors of the compounds of this invention:

1.1. Synthesis of the ionophoric moiety of the diaza-cryptands of the invention (Figure A)

General Process (Figure A)

The synthetic pathway for the ionophoric moiety of the diaza-cryptands of the invention is represented generally in Figure A 2-nitrophenol A1 was reacted with 2-chloroethanol in n-butanol and sodium hydroxide to give 2'-(2'-hydroxyethoxy)nitrobenzene A2. By reducing this compound with $Sn/SnCl_2HCl$, the 2-(2-hydroxyethoxy)aniline A3 was obtained which then with 2-chloroethanol and with 2-(2-chloroethoxy)ethanol, respectively, in dimethylformamide in the presence of triethylamine yielded the N-alkylated aniline derivatives A4 with p=0 and p=1, respectively. By warming 4-toluenesulfonamide A5 with 2-chloroethanol in dimethylformamide and potassium carbonate, the N,N-bis(2-hydroxyethyl)-4-toluenesulfonamide A6 was obtained which then with 4-toluenesulfonic acid chloride yielded the corresponding ditosylate A7.

The ditosylate A7 was then reacted with the N-alkylated aniline derivatives A4 with p=0 and p=1, respectively, in t-butanol/tetrahydrofuran and potassium-t-butoxide as the base to give the corresponding diaza-crown ether toluenesulfonamides A8 with p=0 and p=1, respectively. The pure products were obtained through column chromatography on silica gel. Splitting off of the tosyl group was with lithium aluminum hydride in tetrahydrofuran under reflux, wherein the diaza-crown ethers A9 with p=0 and p=1, respectively, were obtained. 3-oxapentane-dicarboxylic acid dichloride A10 with o=0 and 3,6-dioxaoctanedicarboxylic acid dichloride A10 with o=1 were obtained from the corresponding dicarboxylic acids with oxalic acid dichloride in benzene. The cryptand-bis-amides A11 with o=0, p=0 and o=0, p=1, respectively, were prepared under heavy dilution from the diaza-crown ethers A9 with p=0 and p=1, respectively, by reaction with 3-oxapentane dicarboxylic acid dichloride A10 with o=0 in tetrahydrofuran. The cryptand-bis-amides A11 with o=1, p=0 and o=1, p=1, respectively, were obtained in analogous manner from the diaza-crown ethers A9 with p=0 and p=1, respectively, with 3,6-diazaoctane-dicarboxylic acid dichloride A10 with o=1. Reduction of the amide groups with borane-tetrahydrofuran complex in tetrahydrofuran yielded the diaza-cryptands A12 with o=0, p=0 and o=0, p=1, respectively, and o=1, p=0 and o=1, p=1, respectively.

Introduction of the aldehyde function was through direct formylation with phosphorus oxytrichloride in dimethylformamide, wherein the corresponding diaza-cryptand-aldehydes A13 with o=0, p=0 and o=0, p=1, respectively, and o=1, p=0 and o=1, p=1, respectively. were obtained.

In analogous manner it is feasible to obtain compounds A13 in which o and p independently also mean the number 2.

Description of individual reaction steps of Figure A 2-(2-hydroxyethoxy)nitrobenzene A2:

10 g (71.88 mmol) 2-nitrophenol A1 and 3.59 g (89.86 mmol) sodium hydroxide were dissolved in 55 ml n-butanol and 5 ml water at 70° C., 6.26 ml (7.52 g, 93.44 mmol) 2-chloroethanol were slowly added drop by drop. This was followed by three days of vigorous stirring at 100° C. After cooling, the reaction mixture was filtrated, the precipitate washed with chloroform and the filtrate reduced. The residue was taken up in chloroform and washed three times with aqueous 10% sodium hydroxide solution. Then the organic phase was dried over sodium sulfate and was concentrated in vacuo. 10.8 g of bright yellow crystals were obtained; yield 82%.

$^1$H NMR ($CDCl_3$), δ (ppm): 3.97 (m, 3H), 4.22 (t, 2H), 6.98–7.13 (m, 2H), 7.52 (m, 1H), 7.83 m, 1H).

2-(2-hydroxyethoxy)aniline A3:

8.9 g (48.59 mmol) 2-(2-hydroxyethoxy)nitrobenzene A2, 16.44 g (72.88 mmol) $SnCl_2·2H_2O$ and 17.3 g (145.77 mmol) tin were stirred in 30.84 ml aqueous HCl (30%) and 25 ml water at 90° C. for 8 hours. After cooling, the solution was treated with aqueous 5n sodium hydroxide solution and stirred for 3 hours at 90° C. The aqueous solution was subsequently decanted, wherein, upon cooling, the crude product crystallized out and was removed by suction. This crude product was then taken up in methanol, warmed and the suspension was filtered. The filtrate was then concentrated in vacuo. 6 g of light-brown crystals were obtained; yield 80%.

$^1$NMR ($CDCl_3$), δ (ppm): 3.62 (m, 3H), 3.97 (t, 2H), 6.52–6.75 (m, 4H).

N-[2-(2-hydroxyethoxy)ethyl]-2-(2-hydroxyethoxy) aniline A4 (p=1): 6 g (39.17 mmol) 2-(2-hydroxyethoxy) aniline A3, 5 ml (5.85 g, 47 mmol) 2-(2-chloroethoxy) ethanol and 8.19 ml (5.95 g, 58.75 mmol) triethylamine were dissolved in 20 ml dimethylformamide and stirred for 4 days at 90° C. After cooling, the solution was filtered, the precipitate washed with dichloromethane and the filtrate concentrated in vacuo. The residue was taken up in chloroform and washed twice with a small quantity of water. The chloroform solution was then dried over sodium sulfate and concentrated. The viscous crude product was purified by column chromatography on silica gel 60 with toluene/acetone 1:2 as the mobile phase. 5 g of brown, viscous oil were obtained; yield 53%.

$^1$H NNR ($CDCL_3$), δ (ppm): 3.26 (m, 2H), 3.52 (m, 2H), 3.67 (m, 4H), 3.83 (m, 2H), 4.00 (m, 2H), 4.56 (br s, 2H), 6.55–6.95 (m, 4H).

N,N-bis(2-hydroxyethyl)-4-toluenesulfonamide A6:

6.84 g(40 mmol) 4-toluenesulfonamide A5, 7 ml (8.37 g, 104 mmol) 2-chloroethanol and 27.64 g(200 mmol) potassium carbonate were suspended in 100 ml dimethylformamide and stirred for 3 days at 110° C. Upon cooling, the reaction mixture was filtrated and the precipitate washed with chloroform. The filtrate was concentrated, the oily residue taken up in chloroform and finally washed with a 10% sodium hydroxide solution. On concentrating the organic solution, 8.4 g of pure product were obtained as light yellow crystals; yield: 81%.

$^1$H NMR ($CDCL_3$), δ (ppm): 2.39 (s, 3H), 3.21 (t, 4H), 3.82 (t, 4H), 4.50 (br s, 2H) 7.29 (d, 2H), 7.65 (d, 2H).

N,N-bis(2-hydroxyethyl)-4-toluenesulfonamide-bis-toluenesulfonate A7:

4.54g (17.5 mmol) N,N-bis(2-hydroxyethyl)-4-toluenesulfonamnide A6 were dissolved in 20 ml acetone and cooled down to −5° C. Then, 8 g (42 mmol) 4-toluenesulfonic acid chloride were added, followed by stirring for 10 min. An aqueous 25 % sodium hydroxide solution was slowly added drop by drop at −2° C., then stirring was continued for 8 hours at 0° C. and the reaction mixture placed in a refrigerator overnight. The mixture was poured onto ice-water, with the product precipitating as a viscous oil. The aqueous phase was carefully decanted, the product taken up in chloroform and washed with water. On concentration of the solvent, 9.2 g of pure product were obtained as a light yellow viscous oil which slowly crystallized in the cold; yield: 92%.

$^1$H NMR (CDCL$_3$), δ (ppm) : 2.41 (s, 3H), 2.46 (s, 3H), 3.36 (t, 4H), 4.10 (t, 4H), 4.50 (br s, 2H), 7.29 (d, 2H), 7.34 (d, 4H), 7.62 (d, 2H), 7.76 (d, 4H).

Diaza-crown ether toluenesulfonamide A8 (p=1):

5 g (20.72 mmol) aniline derivative A4 (p=1) and 6.05 g (53.88 mmol) potassium-t-butoxide were dissolved in 280 ml t-butanol under a nitrogen atmosphere and stirred for 2 hours at 60° C. Then, 11.76 g (20.72 mmol) toluenesulfonate A7 in 140 ml dry tetrahyrofuran were added dropwise over a period of 2 h at 40° C. The reaction mixture was subsequently stirred for 48 hours at 60° C. After cooling, the solution was filtered, the precipitate washed with dichloromethane and the filtrate concentrated in vacuo. The residue was dissolved in chloroform and washed with water twice. Finally the organic solution was concentrated, with a dark oily residue forming. From the latter, the product was obtained through column chromatography on silica gel, using toluene/acetone 10:9 as the mobile phase: 1 g of yellow, viscous oil; yield: 10%.

$^1$H NMR (CDCL$_3$), δ (ppm): 2.40 (s, 3H), 3.20–4.50 (m, 20H), 6.55–6.96 (m, 4H), 7.27 (d, 2H), 7.67 (d, 2H).

Diaza-crown ether A9 (p=1):

0.41 g (10.8 mmol) lithium aluminum hydride were suspended in 10 ml dry tetrahydrofuran under a nitrogen atmosphere and 0.5 g (1.08 mmol) diaza-crown ether toluenesulfonamide A8 (p=1) in 10 ml tetrahydrofuran were slowly added drop by drop. The reaction mixture was stirred under reflux for 3 days. After cooling, excess lithium aluminum hydride was decomposed using tetrahydrofuran/water 2:1 (v/v), filtered and the precipitate washed with dichloromethane. The residue was taken up in dichloromethane, filtered and the solvent removed in vacuo. 0.25 g of light-brown oil were obtained; yield: 75%.

Cryptand-bis-amide A11 (o=1, p=1):

This reaction was carried out according to the method of R. Crossley, Z. Goolamali, P. G. Sammes, J. Chem. Soc. Perkin Trans. 2, 1994, 1615–1622. The dicarboxylic acid dichloride A10 (o=0) was obtained by the method of B. Dietrich, J. M. Lehn, J. P. Sauvage, J. Blanzat, Tetrahedron 1973, 29, 1629–1645.

A solution of 0.13 g (1.67 mmol) pyridine in 240 ml dry tetrahydrofuran was prepared and cooled down to 0° C. Subsequently, 0.25 g (0.805 mmol) diaza-crown ether A9 (p=1) in 40 ml dry tetrahydrofuran and 0.17 g (0.605 mmol) 3,6-dioxaoctane dicarboxylic acid dichloride A10 (o=1) in 40 ml dry tetrahydrofuran were added simultaneously in dropwise manner over a period of 4 hours. The reaction mixture was then stirred for another 40 hours at 0° C. The mixture was filtered and the tetrahydrofuran removed. The oily, brown residue was dissolved in chloroform, washed with diluted HCl and then with water. The chloroform solution was dried over sodium sulfate and concentrated. An oily, light-brown. residue was obtained; yield: 0.12 g (33%).

Diaza-cryptand A12 (o=1, p=1):

0.12 g (0.27 mmol) cryptand-bis-amide A11 (o=1, p=1) were placed in a three-necked flask provided with a nitrogen supply, a septum and a reflux cooler with calcium-chloride tubes. 2.5 ml dry tetrahydrofuran were added through the septum by means of a syringe and the suspension was cooled in an ice bath. Then, 2.2 ml (2.2 mmol) of 1 m borane-THF-complex solution were added cautiously, also through the septum. After 10 min, the ice bath was removed, the reaction mixture was stirred at room temperature for 30 min and subsequently under reflux for 2 hours. After cooling, the mixture was cautiously mixed with 1 ml water and 10 ml aqueous 6 n HCl and stirred for 1 hour at room temperature. The solvent was removed in vacuo and the resulting white suspension adjusted to pH 10 with an aqueous lithium hydroxide solution. The aqueous phase was extracted with chloroform. On concentrating the solution in vacuo, a light-brown oil was obtained; yield: 0.1 g (88%).

Diaza-cryptand-aldehyde A13 (o=1, p=1):

A solution of 0.5 g (1.18 mmol) diaza-cryptand A12 (o=1, p=1) in 1.5 ml dimethylformamide was prepared and cooled to −10° C. 0.22 ml (0.36 g, 2.35 mmol) phosphorus oxytrichloride were added cautiously drop by drop so that the temperature did not exceed 0° C. The reaction mixture was stirred for 15 min at −5° C., then at room temperature overnight and, finally, for 1 hour at 60° C. After cooling, the mixture was mixed with water, adjusted to pH 9 with an aqueous concentrated lithium hydroxide solution and was stirred for 30 min. The solution was extracted 3 times using 30 ml chloroform in each case and the organic phase was concentrated in vacuo. 0.32 g of yellow oil were obtained; yield: 60%.

1.2. Starting products for preparing the pH indicators of the invention (Figure B)

The starting products for preparing the pH indicators of the invention are presented in Figure B. The starting products in question are the compounds $C_1$ to $C_5$ in which the group $R_8$ means —$(CH_2)_n CH_3$, where n may be an integer from 0 to 20.

The compounds $C_1$ and $C_2$ are commercially available. The method for preparing the compounds $C_3$, $C_4$ and $C_5$ is known (M C Angelastro, L E Baugh, T M Chen, J. Med. Chem. 37, 4538–4553, 1994 and H Wang, D D Weller, Tetrahedron Lett. 32, 7385–7388, 1991 and Foye, Fedor, J. Pharm. Assoc. 48, 412, 1959, respectively).

2. Synthesis of compounds of this invention 2.1. General Synthesis (Scheme C)

2.1.1. Synthetic pathway 1 (symmetrically substituted derivatives D8)

An aldehyde D1 in which Y represents the ionophoric moiety of the general Formula (II) or one of the groups

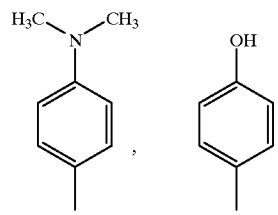

i.e. the compound A13, C1 or C2, and the pyrrole derivative D4 were dissolved in an organic solvent and mixed with an acid, yielding the compound D6 as an intermediate product. By adding p-chloranil in an appropriate solvent, the compound D7 was obtained by oxidation of D6. In the case of the p-hydroxybenzaldehyde derivatives, the dipyrromethene D7 may be obtained directly from the reaction solution and may even be isolated.

Alternatively, the dipyrromethene D7 may also be prepared by reacting D1 with the iodine compound D12.

Reaction of D7 in order to obtain the symmetrically substituted 4,4-difluoro-4-bora-3a,4a-diaza-s-indacene derivative D8 was effected by alternately adding ethyldiisopropylamine and $BF_3 \cdot Et_2O$ to the reaction solution.

The reaction solution of D8 was washed with water, dried over magnesium sulfate and concentrated in vacuo. After repeated column chromatography on silica gel, the compound D8 of the invention was obtained which could be recrystallized from an appropriate solvent (f.i. chloroform/hexane).

2.1.2. Synthetic pathway 2 (symmetrically substituted derivatives D8)

The above aldehyde D1, in which Y represents the ionophoric moiety of the general Formula (II), was oxidized to give the carboxylic acid D2 and subsequently was converted into the corresponding acid chloride D3. Likewise it was possible to utilize the compound C5 as the compound D2 and convert it into the acid chloride D3.

The acid chloride D3 obtained above and the acid chlorides C3 and C4 were then respectively reacted with the pyrrole derivative D4 to obtain the ketone D5, and through further reaction with D4, D7 was obtained. Conversion of D7 into D8 was effected in the manner already described.

The reaction solution of D8 was washed with water, dried over magnesium sulfate and concentrated in vacuo. After repeated column chromatography on silica gel, the compound D8 of the invention was obtained which could be recrystallized from an appropriate solvent (f.i. chloroform/hexane).

2.1.3. Synthetic pathway 3 (unsymmetrically substituted derivatives D11)

The ketone D5 obtained in the manner described above could be converted to D10 with a pyrrole derivative D9 other than D4. By adding ethyldiisopropylamine and $BF_3 \cdot Et_2O$ to the reaction solution, the unsymmetrically substituted 4,4-difluoro-4-bora-3a,4a-diaza-s-indacene derivative D11 was obtained from D10.

The reaction solution of D11 was washed with water, dried over magnesium sulfate and concentrated in vacuo. After repeated column chromatography on silica gel, the compound D11 of the invention was obtained which could be recrystallized from an appropriate solvent (f.i. chloroforn/hexane).

2.1.4. Synthesis of specific compounds 1,3,5,7-hexamethyl-8-(4-dimethylamino-phenyl)-4,4-difluoro-4-bora-3a,4a-diaza-s-indacene D8:

4 mmol (380 mg) dimethylpyrrole D4 ($R_1$, $R_2$=—$CH_3$) and 2 mmol (298 mg) p-dimethylaminobenzaldehyde C1 were dissolved in 300 ml methylene chloride abs under a nitrogen atmosphere and mixed with 40 µl trifluoroacetic acid. After three hours of stirring at room temperature, a solution of 2 mmol (492 mg) p-chloranil in 200 ml methylene chloride was added, followed by another 30 min of stirring. Then, 3 ml ethyldiisopropylamine and 3 ml $BF_3 \cdot Et_2$ were added and stirred for 15 min. The reaction solution was washed with water, dried over magnesium sulfate, and the solvent was evaporated. After repeated chromatographic purification on silica gel with chloroform, a red solid D8 was obtained which was recrystallized from chloroform/hexane (yield: 270 mg; 37%). m.p.: 233–236° C.

Elemental analysis (in %) calculated/found: C: 68.66/68.40; H: 6.53/6.33; N: 11.44/11.32.

$^1$H NMR (250 MHz, $CDCl_3$, TMS, δ in ppm): 1.49 (s, 6H, $CH_3$), 2.55 (s, 6H, $CH_3$), 3.02 (s, 6H, $N(CH_3)_2$), 5.96 (s, 2H, pyrrole), 6.77 (2H, AA'BB', phenyl), 7.06 (2H, AA'BB', phenyl).

MS (EI-MS, 70 eV): 367 (100%), M$^+$352 (24%), (—$CH_3$), 347 (34%), (—HF).

This luminescence indicator is a suitable pH indicator in the acidic range.

1,3,5,7-tetramethyl-2,6-bis(ethoxycarbonyl)-8-(4-hydroxyphenyl)-dipyrromethene D7:

500 mg (1.71 mmol) 2,4-dimethyl-3-ethoxycarbonyl-5-iodine pyrrol and 104 mg (0.89 mmol) 4-hydroxybenzaldehyde were dissolved in 15 ml ethanol, were mixed with 100 µm HCl conc. and heated under reflux for 30 min, wherein an intensely red solution formed after only a few minutes. At 40° C., 150 ml conc. $NH_3$ and 50 ml $H_2O$ were added. This was followed by 10 min of stirring at room temperature, extraction with 2.0 l $CH_2Cl_2$, drying over $Na_2SO_4$ and freeing from the solvent. This was first followed by chromatography on $SiO_2$ with methanol, recrystallization from methanol/$H_2O$ and chromatography on $SiO_2$ with ethanol:$CH_2Cl_2$=2:1. On subsequent chromatography on $SiO_2$ with ethyl acetate, the product could be obtained by drying in an oil pump vacuum (yield: 120 mg of lustrous dark green fine crystals; 0.28 mmol, 32.3% of the theoretical quantity; decomposition starting at 176° C.).

IR (KBr, u [cm$^{-1}$]: 3254, 2980, 2930, 2859, 1704, 1676, 1602, 1563, 1496, 1440, 1371, 1325, 1258, 1163., 1092, 544.

1,3,5,7-tetrarethyl-2,6-bis(ethoxycarbonylethyl)-8-(4-hydroxyphenyl)-4,4-difluoro-4-bora-3a,4a-diaza-s-indacene D8:

310 mg (0.71 mmol) phenoldipyrromethene were dissolved in 500 ml $CH_2Cl_2$ and mixed with 0.5 ml portions of N,N-diisopropyl-N-ethylamine and $BF_3 \cdot Et_2O$ until no further conversion could be observed on the TLC. This was followed by 1 h of stirring at room temperature, freeing from the solvent, followed by chromatography on $SiO_2$ with ethyl acetate and recrystallization from chloroform/$Et_2O$. After renewed chromatography on $SiO_2$ with EE and drying in an oil pump vacuum, the product could be obtained in a pure condition (yield: 110 mg of orange-colored fine crystals, 0.23 mmol, 23.1% of the theoretical quantity; m.p.: 248–250° C., with decomposition).

$^1$H NMR (250 MHz, $CDCl_3$, TMS, δ in ppm): 7.01 (d, 2H, phenyl-H), 6.99 (d, 2H, phenyl-H), 5.68 (bs, 1H, OH), 4.29 (q, 4H, $OCH_2CH_3$), 2.83 (s, 6H, $CH_3$+$CH_3$), 1.72 (s,6H, $CH_3$+$CH_3$), 1.34 (t, 6H, $OCH_2CH_3$).

This luminescence indicator is a suitable pH indicator in the alkaline range.

8-diaza-cryptand-3,5-bis-(methoxycarbonylethyl)-4,4-difluoro-4-bora-3a,4a-diaza-s-indacene D8 with o=1, p=1, $R_1=R_4$=—$CH_2CH_2$—$COOCH_3$, $R_2=R_3=R_5=R_6$=H, Y=diaza-cryptand A12 with o=1 and p=1:

0.31 g (2 mmol) 2-(2-pyrrolyl)-propionic acid methyl ester D4 and 0.45 g (1 mmol) diaza-cryptand aldehyde A13 with o=1 and p=1 were dissolved under a nitrogen atmosphere in 100 ml dry dichloromethane, stirred for 10 min and mixed with 40 µl trifluoroacetic acid. After 1.5 hours of stirring at room temperature, a solution of 0.49 g (2 mmol) tetrachloro-p-benzoquinone in 20 ml tetrahydrofuran was added. The resulting dark red solution was stirred for another 15 min. Subsequently, 5×1 ml diisopropylethylamine and 5x 1 ml boron trifluoride diethyletherate were added alternately, then stirred for 30 min. The solution was washed with water, dried over sodium sulfate and concentrated in vacuo. The residue was purified through column chromatography on silica gel with chloroformethylacetate 9:1 as the mobile phase, wherein 0.16 g of orange-colored powder (yield: 20%) were obtained.

General description of the hydrolysis of the diesters D8 into dicarboxylic acids:

The diesters D8 (Y=diaza-cryptand A12 with o=1 and p=1) that were obtained were dissolved in tetrahydrofuran and diluted to double the volume with water. The mixture was acidified with concentrated $H_3PO_4$ and stirred at 70° C. for 4 days. This solution was concentrated in vacuo, the residue taken up in chloroform, dried over sodium sulfate and the solvent removed. The residue was then purified through column chromatography on silica gel with chloroform/methanol as the mobile phase. Also, monocarboxylic acid was obtained as a byproduct.

This luminescence indicator is useful for determining physiological concentrations of sodium ions.

Preparation of the monoesters: $R_1$=—$CH_2$—$CH_2$—COO—$CH_3$, $R_4$=—$CH_2$—$CH_2$—COOH, and of the diacids: $R_1$=$R_4$ —$CH_2$—$CH_2$—COOH:

The orange-colored powder obtained in the two previous examples of synthesis was dissolved in 4 ml tetrahydrofuran and then diluted with 6 ml water. Then, 0.3 ml 85% $H_3PO_4$ were added, followed by 4 days of heating at 70° C. The tetrahydrofuran was evaporated and the residue extracted twice with 50 ml chloroform and dried over $K_2SO_4$. The solvent was evaporated, yielding 0.17 g oil. This oil was purified using a column packed with silica gel 100 (eluant: chloroform/methanol; 3:1), yielding 0.04 g monoester and 0.02 g diacid.

The monoester was utilized for measuring the properties in solution, whereas the diacid was immobilized on aminocellulose according to the process set forth below and measured in a sensor, as will be described below.

Preparation of a pH sensitive layer for use in a sensor:

0.1 g dry hydrophilic polymer D5 (Tyndale Plains-Hunter LTD, Ringoes, N.J. 08551) and 1.92 g luminescence indicator were dissolved in 1.8 g ethanol and 0.23 g water. The mixture was vigorously stirred at room temperature overnight. 100 µl of this solution were coated on a dustfree 125 mm polyester carrier having a width of 25 mm (Goodfellow; Cambridge; Prod. No. LS 146585). On evaporating the ethanol, a pH sensitive layer having a thickness of 10 µm was obtained on the polyester carrier. From this carrier, a disc was cut out for a sensor.

To condition the polymer, the obtained sensor disc was stored in a 100 mmol/l NaCl solution for 2 hours.

Preparation of an $Na^+$, $K^+$ sensitive layer for use in a sensor:

0.03 mequ. of the diacid indicator, 0.06 g (0.3 mmol) N,N-dicyclohexyl-1,3-carbodiimide, 0.04 g (0.3 mmol) N-hydroxysuccinimide and 0.5 g activated cellulose (prepared in accordance with SU-A-1,028,677, CA 99:177723h) were suspended in 2 ml dimethylformamide for 20 hours. The cellulose was then filtered off, washed 5 times with 5 ml dimethylformamide, 5 ml water, twice with 5 ml 0.2 n HCl, 5 ml water, twice with 5 ml 0.2 n NaOH, 10 times with 5 ml water, twice with 5 ml acetone and twice with 5 ml ether, and was dried for 16 hours at room temperature. Subsequently, the cellulose was sieved (25 µm).

Sensor discs were produced in the following manner:

0.25 g sieved (25 µm) aminocellulose fibers with an immobilized indicator were suspended in 4.75 g 10% hydrogel D4 (Tyndale Plains-Hunter LTD. Ringoes, N.J. 08551) in 90% ethanol-water for 16 hours. The resulting homogenous dispersion was applied to a polyester foil (Goodfellow; Cambridge; Prod. No. LS 146585) up to a dry density of 10 µm. This foil was coated over with 3% activated carbon in 10% D4 hydrogel up to a dry density of 5 µm, whereupon a small disc 2.5 cm in diameter was cut out. This disc was left in the buffer for at least 16 hours for activation.

A method of cutting and measuring sensor discs was described by M. J. P. Leiner and P. Hartmann in Sensors and Actuators B, 11 (1993), 281-189 ("Theory and Practice in optical pH sensing").

3. Luminescence properties of some compounds of the invention:

FIGS. D to G show the luminescence properties of some indicators of the invention as a function of the pH value and of the given concentrations of alkali ions, respectively. The ordinates of the illustrated diagrams give the relative luminescence intensities.

3.1. Figure D: 4,4-difluoro-4-bora-3a,4a-diaza-s-indacene derivative (general Formula I, with $R_7$=4-dimethylaminophenyl as the pH sensitive, ionophoric moiety; $R_1$, $R_3$, $R_4$ and $R_6$=methyl; $R_2$ and $R_5$=H)

Using the compound shown in Figure D, a sensor disc with a pH sensitive layer was prepared, and the pH-dependent luminescence intensity was measured in a set-up described by M. J. P. Leiner and P. Hartmann in Sensors and Actuators B 11; 281–289, 1993.

The measuring set-up is represented schematically in Figure H, where S denotes a portion of the sensor disc. The compound dissolved in the hydrophilic ion-permeable polymer (hydrogel) is denoted by I. This layer M is carried by a carrier T permeable to excitation and measuring radiation, which is a transparent foil.

According to the invention, the compound I can also be bound to the ion-permeable matrix directly in a covalent manner or it can be present in the matrix in physically dissolved condition.

For measurement, the sensor disc was introduced into a thermostatted through-flow cell impervious to light and was contacted with samples P, which contained 0.1 mol/l NaCl and exhibited different pH values. The pH values of the samples were determined using a standard glass electrode.

The optical measuring system consisted of a blue LED as the light source A, a photodiode M as the detector, optical filters A and F for selecting the wavelengths, a fiber-optic arrangement for conducting the excitation light into the polymer M and for conducting the emission light to the photodetector M as well as a device for electronic signal processing (not illustrated). At the excitation end there was utilized an interference filter (peak transmission at 480 nm) and at the emission end a 520 nim cut-off filter.

The curve shown in Figure D thus represents a pH titration curve.

3.2. Figure E: 4,4-difluoro-4-bora-3a,4a-diaza-s-indacene derivative (general Formula I, with $R_7$=—($CH_2$)-morpholino as the pH-sensitive, ionophoric moiety; $R_1$, $R_3$, $R_4$ and $R_6$ methyl; $R_2$ and $R_5$=H)

The example presented in Figure D was repeated, except that the abovementioned morpholino derivative was used and measurement was conducted at different pH values.

3.3. Figure F: 4,4-difluoro-4-bora-3a,4a-diaza-s-indacene derivative (general Formula I, with $R_7$=4-hydroxyphenyl as the pH-sensitive, ionophoric moiety; $R_1$, $R_3$, $R_4$ and $R_6$=methyl; $R_2$ and $R_5$=—COO—$CH_2$—$CH_2$—$CH_3$)

The example presented in Figure D was repeated, except that the abovementioned hydroxyphenyl derivative was used and measurement was conducted at different pH values.

3.4. Figure G: 4,4-difluoro-4-bora-3a,4a-diaza-s-indacene derivative (general Formula I, with $R_7$=cryptand as the $K^+$-sensitive, ionophoric moiety; $R_2$, $R_3$, $R_5$ and $R_6$ =H; $R_1$ and $R_4$=—$CH_2$—$CH_2$—COO—NH-polymer)

Figure G was obtained in a manner analogous to Figure E, but utilizing the recited $K^+$indicator instead of the $Na^+$ indicator and measuring the luminescence intensity as a function of different concentrations of potassium ions (abscissa; logarithmic scale) in the presence of 0.145 mol/l NaCl.

We claim:

1. Compound having the general Formula I

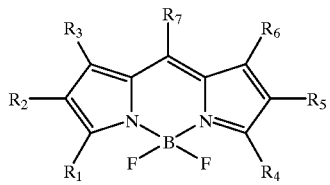

(I)

in which one of the groups $R_1$, $R_2$, $R_3$, $R_4$, $R_5$, $R_6$ and $R_7$ represents an ionophoric moiety and the remaining groups each independently are hydrogen, a lipophilic or hydrophilic group or a reactive group for coupling to a polymer or a biomolecule, or $R_2$ forms an aromatic ring system together with $R_3$ and $R_5$ forms an aromatic ring system together with $R_6$.

2. Compound according to claim 1 wherein $R_7$ is an ionophoric moiety and $R_3$ and $R_6$ are independently hydrogen or methyl.

3. Compound according to claim 1 wherein $R_1$ and $R_4$ are each a lipophilic group.

4. Compound according to claim 1 wherein o and p are each 1.

5. Compound according to claim 2 wherein $R_1$ and $R_4$ are a lipophilic group.

6. Compound according to claim 1 wherein $R_1$ and $R_4$ are each a tertiary butyl group.

7. Compound according to claim 2 wherein $R_1$ and $R_4$ are each a tertiary butyl group.

8. Compound according to any one of claims 1, 2, 3, 4, 5 or 6 wherein the ionophoric moiety is a diaza-cryptand having the general formula II

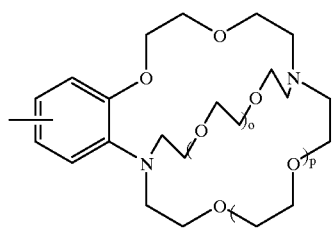

(II)

in which o and p independently is 0, 1 or 2 or is one selected from the following groups

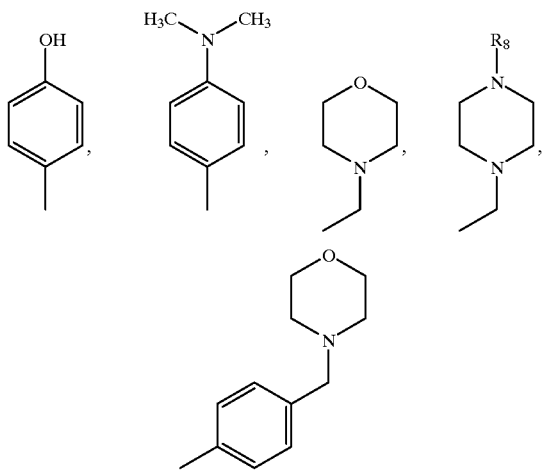

wherein $R_8$=alkyl with 1–20 carbon atoms.

9. Compound according to claim 8 wherein o and p are zero.

10. Compound according to claim 8 wherein o and p are different and selected from the group of 0 and 1.

11. Method for detecting lithium ions in a sample comprising the steps of:

contacting the sample with a luminescence indicator comprising a compound according to claim 5;

measuring the luminescence of the luminescence indicator; and detecting the presence of lithium in the sample based on the measured luminescence.

12. Method for detecting sodium ions in a sample comprising the steps of:

contacting the sample with a luminescence indicator comprising a compound according to claim 6;

measuring the luminescence of the luminescence indicator; and detecting the presence of sodium in the sample based on the measured luminescence.

13. Method for detecting potassium ions in a sample comprising the steps of:

contacting the sample with a luminescence indicator comprising a compound according to claim 7;

measuring the luminescence of the luminescence indicator; and detecting the presence of potassium in the sample based on the measured luminescence.

* * * * *

UNITED STATES PATENT AND TRADEMARK OFFICE
CERTIFICATE OF CORRECTION

PATENT NO. : 6,001,999
DATED : December 14, 1999
INVENTOR(S) : Wolbeis et al

It is certified that error appears in the above-identified patent and that said Letters Patent is hereby corrected as shown below:

Column 2, line 17: "f.i." should read -- e.g. --;

Column 3, line 19: "f.i." should read -- e.g. --;

Column 3, line 25: "f.i." should read -- e.g. --;

Column 3, line 27: "f.i." should read -- e.g. --;

Column 3, line 28: "f.i." should read -- e.g. --;

Column 3, line 29: "f.i." should read -- e.g. --;

Column 4, line 65: "f.i." should read -- e.g. --;

Column 6, line 36: "$^1$NMR" should read -- $^1$H NMR --;

Column 6, line 52: "$^1$H NNR" should read -- $^1$H NMR --;

Column 7, line 3: "4.54 g" should read -- 4.54 g --;

Column 9, line 14: "f.i." should read -- e.g. --;

Column 9, line 33: "f.i." should read -- e.g. --;

Column 9, line 47: "f.i." should read -- e.g. --;

Column 10, line 23: "Sio$_2$" should read -- SiO$_2$ --;

UNITED STATES PATENT AND TRADEMARK OFFICE
CERTIFICATE OF CORRECTION

PATENT NO. : 6,001,999
DATED : December 14, 1999
INVENTOR(S) : Wolbeis et al

It is certified that error appears in the above-identified patent and that said Letters Patent is hereby corrected as shown below:

Column 10, line 28: "1163.," should read
-- 1163, --;

Column 10, line 30: "-tetrarethyl-" should read -- -tetramethyl- --;

Column 13, line 32: "claim 1" should read
-- claim 8 --;

Column 13, line 40: "4, 5" should read
-- 5, 6 --;

Column 13, line 41: "or 6" should read
-- or 7 --;

Column 13, line 42: "formula II" should read --
Formula II --;

Signed and Sealed this

Tenth Day of April, 2001

Attest:

NICHOLAS P. GODICI

*Attesting Officer*      *Acting Director of the United States Patent and Trademark Office*